US011938190B2

(12) United States Patent
Bomstein et al.

(10) Patent No.: US 11,938,190 B2
(45) Date of Patent: Mar. 26, 2024

(54) HERBAL EXTRACTS FOR TREATMENT OF HERPESVIRUS INFECTIONS

(71) Applicant: KAMEDIS LTD., Tel Aviv (IL)

(72) Inventors: Yonit Bomstein, Petach Tikwa (IL); Jonathan Marder, Rechovot (IL); Tali Pechenick Jowers, Raanana (IL)

(73) Assignee: KAMEDIS LTD, Tel Aviv (IL)

( * ) Notice: Subject to any disclaimer, the term of this patent is extended or adjusted under 35 U.S.C. 154(b) by 104 days.

(21) Appl. No.: 16/959,174

(22) PCT Filed: Dec. 30, 2018

(86) PCT No.: PCT/IL2018/051409
§ 371 (c)(1),
(2) Date: Jun. 30, 2020

(87) PCT Pub. No.: WO2019/135215
PCT Pub. Date: Jul. 11, 2019

(65) Prior Publication Data
US 2020/0397908 A1  Dec. 24, 2020

Related U.S. Application Data

(60) Provisional application No. 62/612,724, filed on Jan. 2, 2018.

(51) Int. Cl.
| | | |
|---|---|---|
| *A61K 47/46* | (2006.01) | |
| *A61K 9/00* | (2006.01) | |
| *A61K 9/06* | (2006.01) | |
| *A61K 31/522* | (2006.01) | |
| *A61K 47/10* | (2017.01) | |
| *A61K 47/22* | (2006.01) | |

(52) U.S. Cl.
CPC ............ *A61K 47/46* (2013.01); *A61K 9/0014* (2013.01); *A61K 9/06* (2013.01); *A61K 31/522* (2013.01); *A61K 47/10* (2013.01); *A61K 47/22* (2013.01)

(58) Field of Classification Search
None
See application file for complete search history.

(56) References Cited

U.S. PATENT DOCUMENTS

| 4,985,247 A | * | 1/1991 | Liu ...................... A61K 36/315 |
| | | | 424/773 |
| 2009/0035401 A1 | * | 2/2009 | Turner ..................... A61P 31/16 |
| | | | 424/764 |
| 2013/0323335 A1 | * | 12/2013 | Rozenblat ............ A61K 36/739 |
| | | | 424/741 |

FOREIGN PATENT DOCUMENTS

| CN | 103202790 | 7/2013 |
| KR | 2017 0022348 | 3/2017 |
| WO | WO 2007/136773 | 11/2007 |
| WO | WO 2014/041542 | 3/2014 |
| WO | WO-2014041542 A2 | * 3/2014 | ........... A61K 36/185 |
| WO | WO 2018/087766 | 5/2018 |

OTHER PUBLICATIONS

Cheng et al (Anti-inflammatory and immunomodulatory activities of the extracts from the inflorescence of Chrysanthemum indicum Linne. Journal of Ethnopharmacology 101 (2005) 334-337) (Year: 2005).*
Chung et al (Potential Antiviral Effects of Terminalis chebula, Sanguisorba officinalis, Rubus coreanus and Rheum palmatum against Duck Hepatitis B Virus (DHBV). Phytotherapy Research, vol. 11, 179-182 (1997)) (Year: 1997).*
Shiqiang Deng et al; Topical Herbal Formulae in the Management of Psoriasis: Systematic Review with Meta-Analysis of Clinical Studies and Investigation of the Pharmacological Actions of the Main Herbs; Topical Herbal Formulae for Psoriasis; Phytotherapy Research; vol. 28, No. 4, Apr. 1, 2014; pp. 480-497.
Chattopadhyay Deprasad et al; Ethnomedicines and ethnomedicinal phytophores against herpesviruses, BIOTECHNOLOGY Annual Review, Elsevier, NL, vol. 14, Jan. 1, 2008, pp. 297-348.
European Search Report dated Sep. 30, 2021 for corresponding Application No. EP18898322.5.
International Search Report and Written Opinion for PCT Application No. PCT/IL2018/051409, dated Apr. 22, 2019.
Ping Zhou et al; A Comprehensive Review of Genus *Sanguisorba*: Traditional Uses, Chemical Constituents and Medical Applications; Frontiers in Pharmacology; vol. 12 | Article 750165; Sep. 20, 2021.
Alexandra-Cristina Tocai; Evaluation of Polyphenolic Composition and Antimicrobial Properties of *Sanguisorba officinalis* L. and *Sanguisorba minor* Scop.; Plants 2022, 11, 3561; Published: Dec. 16, 2022.
Mohammad Najmul Ghani Khan Khazaain-al-Advia, vol. II (20th century AD), Nadeem Yunus Printer Sheikh Mohd Basheer & Sons, Labore 1911, AD p. 668, Formulation ID: AN2672C, Formulation Name: Zimaad-e-Reebaas Barae Surkhbaada.
Mahendra Bhaugika Dhanvantarinighantauh, edited by P.V. Sharma: translated by Guru Prasad Sharma, Chaukhambha Orientalia, Varanasi, Edn. 3rd, 2002, p. 175; Sodhala Sodhalanighantauh, edited by P.V. Sharma, Oriental Institute, Baroda, Edn. 1st 1978, p. 136, Formulation ID: AK12/425, Formulation Name: Satapatri Guna.
Mohammad Azam Khan Muheet-e-Azam, vol. II, (19th century AD) Matba Nizami, Kanpur, 1887 AD, p. 64, Formulation ID: JA7/82A, Formulation Name: Zimaad-e-Sandreetas.

(Continued)

*Primary Examiner* — Jake M Vu
(74) *Attorney, Agent, or Firm* — PEARL COHEN ZEDEK LATZER BARATZ LLP (57) ABSTRACT

Disclosed is a formulation comprising at least two of *Rheum palmatum*, *Chrysanthemum indicum* and *Sanguisorba officinalis* extracts or prevalent molecules therefrom and a pharmaceutically acceptable carrier. Further disclosed is a formulation comprising one or more of *Rheum palmatum*, *Chrysanthemum indicum* and *Sanguisorba officinalis* extracts, or prevalent molecules therefrom in combination with acyclovir and a pharmaceutically acceptable carrier. Disclosed also is a method for treating herpesvirus infections by administering a formulation comprising extracts of *Rheum palmatum*, *Chrysanthemum indicum* or *Sanguisorba officinalis* extracts or prevalent molecules therefrom with or without an antiviral agent, such as acyclovir and a pharmaceutically acceptable carrier.

12 Claims, 9 Drawing Sheets

(56) References Cited

OTHER PUBLICATIONS

Mohammad Najmul Ghani Khan Khazaain-al-Advia, vol. II (20$^{th}$ century AD), Nadeem Yunus Printer Sheikh Mohd Basheer & Sons, Lahore, 1911, AD p. 858, Formulation ID: AN2/857D, Formulation Name: Zimad-e-Sandreetas/sameeqa.

* cited by examiner

Self-assessment by subjects with oral herpes, treated with formulations comprising herbal extracts

| # | Gender | Rheum palmatum : Sanguisorba officinalis : Chrysanthemum indicum | Application /day | Treatment duration (days) | Redness | Blister development | Wound development | Comment |
|---|---|---|---|---|---|---|---|---|
| 1 | F | 1:1:0 | 3 | 1 | eliminated | no | no | |
| 2 | M | 1:1:0 | 1 | 3 | reduced | reduced | no | |
| 2 | M | 1:1:0 | 1 | 3 | eliminated | eliminated | no | |
| 3 | M | 1:1:0 | ND | ND | ND | ND | ND | no difference between Zoverax and the treatment (condition duration) |
| 4 | M | 1:1:0 | 1 | 1 | no | no | no | |
| 6 | M | 1:1:0 | 3 | 1 | no | no | no | |
| 1 | F | 1:1:20 | 3 | 1 | eliminated | no | no | |
| 2 | M | 1:1:20 | 1 | 3 | eliminated | eliminated | no | |
| 5 | M | 1:1:20 | 3 | 1 | eliminated | no | no | |
| 6 | M | 1:1:20 | 3 | 1 | no | no | no | |
| 7 | M | 1:1:20 | 2 | 1 | eliminated | reduced | no | |
| 1 | F | 1:1:4 | 3 | 2 | eliminated | reduced | no | |
| 2 | M | 1:1:4 | 1 | 3 | eliminated | eliminated | no | |
| 5 | M | 1:1:4 | 3 | 1 | eliminated | no | no | |
| 6 | M | 1:1:4 | 3 | 1 | no | no | no | |
| 7 | M | 1:1:4 | 4 | 1 | eliminated | small blistered appeared | no | |
| 8 | F | 1:1:4 | 1 | 1 | no | no | no | |

HERBAL EXTRACTS FOR TREATMENT OF HERPESVIRUS INFECTIONS

CROSS-REFERENCE TO RELATED APPLICATIONS

This application is a National Phase Application of PCT International Application No. PCML2018/051409, International Filing Date Dec. 30, 2018, entitled "HERBAL EXTRACTS FOR TREATMENT OF HERPESVIRUS INFECTIONS", published on Jul. 11, 2019 as International Patent Application Publication No. WO 2019/135215, claiming the benefit of U.S. Provisional Patent Application No. 62/612,724, filed Jan. 2, 2018, which is incorporated herein by reference in its entirety.

FIELD OF THE INVENTION

The invention is directed to formulations comprising different mixtures of herbal extracts together with additional ingredients. The invention is further directed to the use of such formulations for the treatment of diseases resulting from herpesvirus infections, including oral herpes (such as cold sores), genital herpes and shingles.

BACKGROUND OF THE INVENTION

Viruses are small forms of heritable material that replicate by infecting the living cells of other organisms and exploiting their cellular machinery. Viruses infect all life forms, including humans. In some cases the infection can be asymptomatic, while in others there may be symptoms that range in severity from relatively mild (as in the case of common cold) to extremely severe (as in diseases such as smallpox).

Herpesviridae is a large family of enveloped DNA viruses of which eight are known to infect and cause disease in humans: herpes simplex virus 1 (HSV-1, HHV1), herpes simplex virus 2 (HSV-2, HHV2), varicella zoster virus (VZV; HHV3), Epstein-Barr virus (EBV; HHV4), cytomegalovirus (CMV; HHV5), human herpesvirus 6 (HHV6), human herpesvirus 7 (HHV7) and Kaposi's sarcoma-associated herpesvirus (KSHV; HHV8). These viruses are distributed globally, and importantly, establish a lifelong latent infection of the host following primary infection.

HSV-1, HSV-2 and VZV belong to the sub-family of alphaherpevirinae. They share most genes and encode similar functions. All three cause diseases of the skin or mucosa, remain dormant in neurons and subsequently reactivate to cause recurrent disease.

HSV-1 and HSV-2 are highly prevalent throughout the world. Following primary infection HSV establish a latent infection in sensory neurons; thereafter, periodical reactivation results in lesions that occur at or near the original point where the virus first entered the body. In 2012 an estimated 67% of the world population had HSV-1 infection. HSV-1 is normally associated with oral herpes, characterized by blisters or sores in or around the mouth that are vernacularly referred to as "cold sores" or "fever blisters". HSV-2 usually causes genital herpes, with estimated prevalence of about 31% and 14% in Africa and the Americas, respectively. Importantly, HSV-1 may cause genital herpes (indeed incidence of HSV-1 related genital herpes in on the rise) and conversely HSV-2 may cause oral herpes.

VZV is the causative agent of chickenpox and shingles. Primary infection with VZV results in chickenpox, after which the virus remains dormant in nerve cells. Reactivation of the virus manifests as shingles a painful rash consisting of blisters. Almost 1 out of 3 people in the United States will develop shingles during their lifetime.

Acyclovir is an antiviral drug used to treat HSV and VZV infections, as well as for preventing post-transplant CMV infection. Acyclovir works by inhibiting viral DNA polymerases, thus preventing viral DNA replication and the creation of new viral progeny.

In the case of conditions related to herpesvirus infections antiviral agents such as acyclovir are established therapies for reducing disease severity. However some of these agents are associated with deleterious side effects. Moreover, long term usage of acyclovir may give rise to resistant viruses, particularly in immunocompromised individuals. Oral herpes treatment is usually topical, with agents such as paracetamol and lidocaine used to alleviate discomfort. However, these treatments do not affect the virus directly.

There is a need for new treatments for herpesvirus infections that provide both symptom relief and antiviral activity with minimal adverse side effects.

SUMMARY OF THE INVENTION

Embodiments of the invention are directed to a formulation comprising extracts of at least two of *Rheum palmatum*, *Chrysanthemum indicum* and *Sanguisorba officinalis*, or prevalent molecules therefrom and a pharmaceutically acceptable carrier.

According to some embodiments, a formulation comprises extracts from at least one of *Rheum palmatum*, *Chrysanthemum indicum* or prevalent molecules therefrom, together with an antiviral agent, for example, acyclovir.

According to some embodiments of the invention, the formulation is a topical formulation.

According to some embodiments, the topical formulation further comprises glycerine, allantoin or any combination thereof. According to some embodiments, the topical formulation further comprises solvents, emollients, moisturizers, conditioners, viscosity modifiers, skin calmers, emulsifiers, pH adjusters, preservatives, antioxidants, viscosity increasing agents, perfumes, colorants, fats, waxes, oils, humectants, stabilizers, detergents or any combination thereof.

According to some embodiments, the pH of the topical formulation is between about 4.0 to about 7.0.

According to some embodiments, the combined concentration of the herbal extracts in the topical formulation is between about 0.1% w/w and about 10% w/w.

Some embodiments of the invention are directed to a method of treating herpesvirus infections by administering the formulation detailed herein.

In some embodiments the formulation may be used to treat one or more of the human diseases herpesviruses are known to cause. HSV-1 infection may result in gingivostomatitis, keratoconjunctivitis, cutaneous herpes, genital herpes, encephalitis, herpes labialis also known as oral herpes, viral meningitis, esophagitis, pneumonia, disseminated infection and hepatitis (the latter four in immunocompromised hosts). In addition, HSV-1 infection of skin regions with eczema may results in eczema herpeticum. HSV-2 infection may result in genital herpes, cutaneous herpes, gingivostomatitis, neonatal herpes, viral meningitis, disseminated infection and hepatitis (the latter two in immunocompromised hosts). Varicella-zoster virus infection may result in chickenpox, herpes zoster also known as shingles, and disseminated herpes zoster (the latter in immunocompromised hosts). Epstein-Barr virus infection may result in infectious mononucleosis, hepatitis, encephalitis, lymphoproliferative syndromes and oral hairy leukoplakia (the latter two in immunocompromised hosts). Infection with Epstein-Barr virus is also associated with nasopharyngeal carcinoma, Hodgkin lymphoma and Burkitt lymphoma. Cytomegalovirus infection may result in cytomegalovirus mononucleosis, hepatitis, congenital cytomegalic inclusion disease, hepatitis, retinitis, pneumonia and colitis (the latter four in immunocompromised hosts). Human herpesvirus 6 infection may result in roseola infantum, otitis media with fever and encephalitis. Human herpesvirus 7 infection may result in roseola infantum. Kaposi sarcoma-associated herpesvirus infection may result in in Kaposi sarcoma and AIDS-related non-Hodgkin lymphomas.

According to some embodiments, the formulation may be administered once, twice, three times a day or more. According to some embodiments, the formulation is administered for between one and ten days or more.

According to some embodiments, the formulation is designed for any route of administration such as, without limitation, topical, ocular, oral, mucosal, enteral, by inhalation or parenteral administration.

DESCRIPTION OF THE DETAILED
EMBODIMENTS OF THE INVENTION

Throughout this application, the term "about" is defined as ±10% of the specifically disclosed value or range. The term % w/w, relates to the percentage by weight of a particular ingredient relative to the entire formulation.

The term "preventing" refers herein to inhibiting progression of a disease, disorder or condition from developing in a subject. In some embodiments, the term "preventing" refers herein to attenuating the onset and development of disease symptoms. In some cases the subject may be at risk for developing the disease, but has not yet been diagnosed as having the disease.

Embodiments of the invention are directed to a formulation that may be a topical formulation, comprising extracts of at least two of *Rheum palmatum, Chrysanthemum indicum* and *Sanguisorba officinalis*, or prevalent molecules therefrom.

According to some embodiments, a formulation, that may be topical, comprising extracts from at least one of *Rheum palmatum* and *Chrysanthemum indicum* or prevalent molecules therefrom, together with an antiviral agent, such as acyclovir is provided.

Examples of prevalent molecules of the respective extracts are provided in Table I below.

TABLE I

| Herb | Prevalent molecules |
| --- | --- |
| *Chrysanthemum indicum* | Buddleoside |
| *Sanguisorba officinalis* | Gallic acid |
| *Rheum palmatum* | Anthraquinones |

According to some embodiments, the formulation further comprises glycerine, allantoin or any combination thereof.

Further embodiments of the invention are directed to the use of a formulation, which may be a topical formulation, comprising extracts of *Rheum palmatum, Chrysanthemum indicum* and *Sanguisorba officinalis*, or prevalent molecules therefrom, for the treatment of diseases resulting from herpesvirus infections, including oral herpes (such as cold sores), genital herpes and shingles.

In some embodiments the formulation may be used to treat one or more of the human diseases herpesviruses are known to cause. HSV-1 infection may result in gingivostomatitis, keratoconjunctivitis, cutaneous herpes, genital herpes, encephalitis, herpes labialis also known as oral herpes, viral meningitis, esophagitis, pneumonia, disseminated infection and hepatitis (the latter four in immunocompromised hosts). In addition, HSV-1 infection of skin regions with eczema may results in eczema herpeticum. HSV-2 infection may result in genital herpes, cutaneous herpes, gingivostomatitis, neonatal herpes, viral meningitis, disseminated infection and hepatitis (the latter two in immunocompromised hosts). Varicella-zoster virus infection may result in chickenpox, herpes zoster also known as shingles, and disseminated herpes zoster (the latter in immunocompromised hosts). Epstein-Barr virus infection may result in infectious mononucleosis, hepatitis, encephalitis, lymphoproliferative syndromes and oral hairy leukoplakia (the latter two in immunocompromised hosts). Infection with Epstein-Barr virus is also associated with nasopharyngeal carcinoma, Hodgkin lymphoma and Burkitt lymphoma. Cytomegalovirus infection may result in cytomegalovirus mononucleosis, hepatitis, congenital cytomegalic inclusion disease, hepatitis, retinitis, pneumonia and colitis (the latter four in immunocompromised hosts). Human herpesvirus 6 infection may result in roseola infantum, otitis media with fever and encephalitis. Human herpesvirus infection may result in roseola infantum. Kaposi sarcoma-associated herpesvirus infection may result in in Kaposi sarcoma and AIDS-related non-Hodgkin lymphomas.

Further embodiments of the invention are directed to the use of a formulation, which may be a topical formulation, comprising extracts of *Rheum palmatum* and *Chrysanthemum indicum* or prevalent molecules therefrom, together with acyclovir, for treatment of diseases resulting from herpesvirus infections, including oral herpes (such as cold sores), genital herpes and shingles.

Further embodiments of the invention are directed to the use of a formulation, which may be a topical formulation, comprising extracts of *Rheum palmatum, Chrysanthemum indicum* and *Sanguisorba officinalis*, or prevalent molecules therefrom, for the treatment of diseases resulting from HSV infections, including oral herpes (such as cold sores) and genital herpes.

Further embodiments of the invention are directed to the use of a formulation, which may be a topical formulation comprising extracts of *Rheum palmatum* and *Chrysanthemum indicum* extracts, or prevalent molecules therefrom together with acyclovir, for treatment of diseases resulting from HSV infections, including oral herpes (such as cold sores) and genital herpes.

Further embodiments of the invention are directed to the use of a formulation, which may be a topical formulation, comprising extracts of *Rheum palmatum, Chrysanthemum indicum* and *Sanguisorba officinalis*, or prevalent molecules therefrom, for the treatment of diseases resulting from VZV infections, including shingles.

Further embodiments of the invention are directed to the use of a formulation, which may be a topical formulation, comprising extracts of *Rheum palmatum* and *Chrysanthemum indicum* or prevalent molecules therefrom, together with acyclovir, for treatment of diseases resulting from VZV infections, including shingles.

The methods and the formulations described herein may be applicable to any disease or condition caused by any member of the herpesviridae family. In some embodiments, the methods and the formulations described herein may be applicable to any disease or condition caused by HSV-1. In some embodiments, the methods and the formulations described herein may be applicable to any disease or condition caused by HSV-2. In some embodiments, the methods and the formulations described herein may be applicable to any disease or condition caused by VZV.

Further embodiments of the invention are directed to the prophylactic use of a formulation, which may be a topical formulation, comprising extracts of at least two of *Rheum palmatum, Chrysanthemum indicum* and *Sanguisorba officinalis*, or prevalent molecules therefrom, to limit the spread of herpesvirus-associated lesions to unaffected areas of skin or mucosa, or to reduce the risk of infecting other individuals. In some embodiments, acyclovir may be further administered in either the same formulation or in a separate formulation.

Further embodiments of the invention are directed to the prophylactic use of a formulation, which may be a topical formulation, comprising at least one of *Rheum palmatum*, and *Chrysanthemum indicum* extracts, or prevalent molecules therefrom, together with acyclovir, to limit the spread of herpesvirus-associated lesions to unaffected areas of skin or mucosa, or to reduce the risk of infecting other individuals. In further embodiments, the acyclovir may be administered in a separate formulation.

According to some embodiments, the total concentration of all of the herbal extracts combined in the formulation, is between about 0.01% w/w and about 50% w/w.

According to some embodiments, the combined concentration of the herbal extracts in the formulation is between about 0.01-0.5% w/w. According to some embodiments, the combined concentration of the herbal extracts in the formulation is between about 0.01-1.0% w/w. According to some embodiments, the combined concentration of the herbal extracts in the formulation is between about 0.01-2.0% w/w. According to some embodiments, the combined concentration of the herbal extracts in the formulation is between about 0.01-3.0% w/w. According to some embodiments, the combined concentration of the herbal extracts in the formulation is between about 0.01-4.0% w/w. According to some embodiments, the combined concentration of the herbal extracts in the formulation is between about 0.01-5.0% w/w. According to some embodiments, the combined concentration of the herbal extracts in the formulation is between about 0.01-6.0% w/w. According to some embodiments, the combined concentration of the herbal extracts in the formulation is between about 0.01-7.0% w/w. According to some embodiments, the combined concentration of the herbal extracts in the formulation is between about 0.01-8.0% w/w. According to some embodiments, the combined concentration of the herbal extracts in the formulation is between about 0.01-9.0% w/w. According to some embodiments, the combined concentration of the herbal extracts in the formulation is between about 0.01-10.0% w/w. According to some embodiments, the combined concentration of the herbal extracts in the formulation is between about 0.01-20.0% w/w. According to some embodiments, the combined concentration of the herbal extracts in the formulation is between about 0.01-50.0% w/w. For any of the formulations detailed above, the extracts may be replaced by their constituent molecules formulated to appropriate concentrations.

According to some embodiments, the ratio between the *Rheum palmatum* and the *Sanguisorba officinalis* extracts is about 1:1.

According to some embodiments, the ratio between the *Rheum palmatum* and the *Sanguisorba officinalis* extracts is about between 2:1 and 1:2. According to some embodiments, the ratio between the *Rheum palmatum* and the *Sanguisorba officinalis* extracts is about between 3:1 and 1:3. According to some embodiments, the ratio between the *Rheum palmatum* and the *Sanguisorba officinalis* extracts is between about 10:1 and 1:10. According to some embodiments, the ratio between the *Rheum palmatum* and the *Sanguisorba officinalis* extracts is between about 100:1 and 1:100. According to some embodiments, the ratio between the *Rheum palmatum* and the *Sanguisorba officinalis* extracts is between about 1000:1 and 1:1000. According to some embodiments, the ratio between the *Rheum palmatum* and the *Sanguisorba officinalis* extracts is between about 5000:1 and 1:5000. For any of the formulations detailed above, the extracts may be replaced by their constituent molecules formulated to appropriate concentrations.

According to some embodiments, extract of *Chrysanthemum indicum* is included in the formulation together with extracts of either *Rheum palmatum* or *Sanguisorba officinalis*, or any mixture of *Rheum palmatum* and *Sanguisorba officinalis* extracts, such that the ratio of *Chrysanthemum indicum* to the total amount of the other herbal extract(s) is between 2:1 and 20:1. According to some embodiments, the ratio of *Chrysanthemum indicum* extract to the total of the other herbal extracts is between 2:1 and 50:1. According to some embodiments, the ratio of *Chrysanthemum indicum* extract to the total of the other herbal extract(s) is between 2:1 and 100:1. According to some embodiments, the ratio of *Chrysanthemum indicum* extract to the total of the other herbal extract(s) is between 2:1 and 200:1. According to some embodiments, the ratio of *Chrysanthemum indicum* extract to the total of the other herbal extract(s) is between 2:1 and 500:1. According to some embodiments, the ratio of *Chrysanthemum indicum* extract to the total of the other herbal extract(s) is between 2:1 and 1000:1. According to some embodiments, the ratio of *Chrysanthemum indicum* extract to the total of the other herbal extract(s) is between 2:1 and 5000:1. For any of the formulations detailed above, the extracts may be replaced by their constituent molecules formulated to appropriate concentrations.

According to some embodiments, acyclovir is included in the formulation together *Rheum palmatum* or a combination *Rheum palmatum* and *Chrysanthemum indicum* extracts, such that the w/w ratio of *Rheum palmatum* extract to acyclovir is between about 10:1 and 1:10. According to some embodiments, the ratio between the *Rheum palmatum* and acyclovir is between about 100:1 and 1:100. According to some embodiments, the ratio between the *Rheum palmatum* and acyclovir is between about 500:1 and 1:500. According to some embodiments, the ratio between the *Rheum palmatum* and acyclovir is between about 1000:1 and 1:1000. According to some embodiments, the ratio between the *Rheum palmatum* and acyclovir is between about 2000:1 and 1:2000. According to some embodiments, the ratio between the *Rheum palmatum* and acyclovir is between about 10000:1-1:10000. For any of the formulations detailed above, the extracts may be replaced by their constituent molecules formulated to appropriate concentrations.

Further embodiments of the invention are directed to the use of a formulation, which may be a topical formulation, comprising *Rheum palmatum, Chrysanthemum indicum* and *Sanguisorba officinalis* extracts, or molecules prevalent therefrom, for treating herpesvirus infections, including oral herpes (such as cold sores), genital herpes and shingles and/or for treating additional maladies present when suffering from herpesvirus infections. The formulation in some embodiments may be used for anti-inflammatory, anti-itch, anti-pain, anti-bacterial and antioxidant treatments. According to other embodiments, formulations described herein may comprise any additional active ingredients, such as anti-inflammatory, anti-itch, anti-pain, anti-viral, anti-bacterial and/or antioxidant agents. In some embodiments, acyclovir may be further administered in either the same formulation or in a separate formulation.

According to some embodiments, any one of the herbal extracts in the formulation may be produced using a polar solvent, such as ethyl alcohol (ethanol), butyl alcohol (butanol), methanol, water, propanol, propylene glycol, butylene glycol, glycerine or any combination thereof. Thus, the herbal extracts may be polar extracts. The polar extracts of the present invention may comprise any percentage of a polar solvent.

According to other embodiments, the plant extracts may be produced by the use of a non-polar solvent, such as isooctane, petroleum ether or any combination thereof. Thus, the herbal extracts may be non-polar extracts. The non-polar extracts of the present invention may comprise any percentage of non-polar solvents.

The active ingredients in the herbal extracts may be purified and concentrated via phase partition and chromatographic methods.

According to some embodiments, the amounts of the organic salts, heavy metals and/or starch in the herbal extract are reduced in comparison to the natural amount of those materials in the plant.

According to some embodiments, the formulation is applied only to the skin or mucosa lesions arising from the herpesvirus infection, e.g., oral herpes, genital herpes or shingles. According to some embodiments, the topical formulation is applied also to the surrounding area of the skin or mucosa affected by the herpesvirus, e.g., the formulation may be applied to about 0.5 or 1.0 cm of additional skin or mucosa in each direction, wherein the center of the application area is the skin or mucosa affected by the herpesvirus infection, e.g., oral herpes, genital herpes or shingles. According to some embodiments, e.g., when used prophylactically, the topical formulation is applied to the entire area of the skin or mucosa where herpesvirus-related symptoms may occur, even if no lesions are evident.

According to some embodiments, any one of the herbal extracts in the formulation, or any of its constituent molecules, may demonstrate synergism with another herbal extract and/or with any additional components in the formulation. According to some embodiments, acyclovir is added to the formulation. According to some embodiments, *Rheum palmatum*, alone or in combination with *Chrysanthemum indicum*, may demonstrate a synergistic effect when combined with acyclovir.

According to some embodiments, the pH of the topical formulation is between about 4.0 to about 7.0. According to some embodiments, the pH of the topical formulation is between about 4.0 to about 5.0. According to some embodiments, the pH of the topical formulation is between about 4.0 to about 6.0. According to some embodiments, the pH of the topical formulation is between about 4.0 to about 7.0. According to further embodiments, the pH of the topical formulation is between about 4.5-6.5. According to further embodiments, the pH of the topical formulation is between about 5.0-6.5.

According to an embodiment of the invention, the compositions of the invention are administered once a day. According to other embodiments, the compositions are administered twice a day, three times a day or more.

According to some embodiments of the invention, the composition is administered for about 1 day, 2 days, 3 days, 5 days, 10 days or more, or any number of days as required.

The composition, which may be in some embodiments a topical formulation, may be in a form of oil-in-water, water-in-oil, water-in-oil-in-water, and oil-in-water-in-silicone emulsions, a cream, an ointment, an aqueous solution, a lotion, a soap, a paste, a foam, an emulsion, a gel, a salve, an oil, a wash, a spray, a conditioner or an aerosol. The topical formulation may be applied in any suitable manner, e.g., by hand, spatula, spray or pad. The topical formulations of the invention show high dermal compatibility and low irritation behavior when applied to human skin or mucosa. According to some embodiments, the formulations are applied to the body and subsequently remove therefrom, e.g., by washing with water.

According to some embodiments of the invention, the formulation may be administered using any appropriate applicator. According to some embodiments, the applicator may include disposable elements, designed in order to prevent contamination, or carryover of the virus.

According to some embodiments of the invention, a formulation may be designed for any other appropriate route of administration such as, without limitation, ocular, oral, mucosal, enteral, by inhalation or parenteral administration.

According to some embodiments, the topical formulation comprises any number of additional ingredients, such as solvents, emollients, moisturizers, conditioners, viscosity modifiers, skin calmers, emulsifiers, pH adjusters, preservatives, antioxidants, viscosity increasing agents, perfumes, colorants, fats, waxes, oils, humectants, stabilizers or any combination thereof.

According to some embodiments, glycerine and/or propylene glycol are added to the plant extracts, e.g., water extracts. The addition of glycerine and/or propylene glycol to the extract may enhance penetration of the formulation into the skin or mucosa and may also aid in preserving the extracts. The extracts may be further protected by addition of any pharmaceutically-acceptable preservative known to those of ordinary skill in the art. Examples of such preservatives include parabens, benzoates, phenoxyethanol and benzalkonium chloride.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch-hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizate), skin treating agents, thickeners, and vitamins and derivatives thereof.

In some embodiments of the invention, there is provided a pharmaceutical composition comprising the herbal extracts or the prevalent molecules therefrom. The pharmaceutical composition may be in a form of a liquid, cream, gel, paste, powder, emulsion, an ointment, a liniment, a lotion, a transdermal system, an injection fluid, a suspension, a patch film patch or spray. In some embodiments, the formulation is in a form of capsule, a tablet, or designed for injection. The composition may be administered in conjunction with one or more additional anti-viral active agent.

As used herein a "pharmaceutical composition" refers to a preparation of the active ingredients described herein with other chemical components such as physiologically suitable carriers and excipients. The purpose of the composition is to facilitate administration of the active ingredients (e.g., the herbal extracts or prevalent molecules therefrom) to the subject.

As used herein the term "active ingredient" refers to the herbal extracts or the prevalent molecules therefrom included for the intended biological eff-ect (i.e., for treatment or prevention of disease, disease symptoms or related conditions resulting from herpesvirus infections).

Hereinafter, the phrases "physiologically acceptable carrier" and "pharmaceutically acceptable carrier" which may be interchangeably used to refer to a carrier or a diluent that does not cause significant irritation to the subject and does not abrogate the biological activity and properties of the administered active ingredients. An adjuvant is included under these phrases.

Herein, the term "excipient" refers to an inert substance added to the composition (pharmaceutical composition or cosmetic composition) to further facilitate administration of an active ingredient of the present invention.

Techniques for formulation and administration of drugs may be found in "Remington's Pharmaceutical Sciences" Mack Publishing Co., Easton, PA, latest edition, which is incorporated herein by reference.

Techniques for formulation and administration may be found in "Remington: The Science and Practice of Pharmacy" Twentieth Edition, Lippincott Williams & Wilkins, Philadelphia, Pa. (1995). For human or animal administration, preparations should meet sterility, pyrogenicity, general safety and purity standards comparable to those required by the FDA. Administration of the pharmaceutical formulation can be performed in a variety of ways, as described herein.

In some embodiments, the pharmaceutical composition is in a form of a solid unit dosage form such as a capsule, tablet and the like, such as an ordinary gelatin type containing the active ingredient thereof of the present invention, and a carrier, for example, lubricants and inert fillers such as, lactose, sucrose, or corn starch. In another embodiment, the active ingredient is tabulated with conventional tablet bases such as lactose, sucrose, or corn starch in combination with binders like acacia, corn starch, or gelatin, disintegrating agents, such as corn starch, potato starch, or alginic acid, and a lubricant, like stearic acid or magnesium stearate. The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the active ingredient can be incorporated with excipients and used in the form of tablets, capsules, elixirs, suspensions, syrups, and the like.

The active ingredient of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

For use as aerosols, the active ingredient thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When administering the active ingredients of the present invention, and pharmaceutical compositions thereof, they can be administered systemically or, alternatively, they can be administered directly to a specific site. Thus, administering can be accomplished in any manner effective for delivering the active ingredients thereof or the pharmaceutical compositions, to the specific targeted cells. Exemplary modes of administration include, without limitation, administering the active ingredients thereof or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Toxicity and therapeutic efficacy of the herbal extracts or their prevalent molecules, or the combination thereof with anti-viral agents described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell-culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the active ingredient of the invention can be formulated or administered together with additional active ingredients as required to treat the condition of the patient.

Alternately, one may administer the composition in a local rather than systemic manner, for example, by injecting the composition including the active ingredient (and a physiologically acceptable carrier) directly into a tissue region of a patient (e.g. to the infected skin or into a healthy skin that surrounds the infected skin).

Suitable routes of administration of the compositions may, for example, include ocular (e.g., to the eye), topical (e.g., to a keratinous tissue, such as the skin, hair, nail, scalp), transdermal, subdermal, pulmonary and oral (e.g., by mouth) administrations.

As used herein the phrase "dermal administration" or "topical administration" refers to applying or spreading the composition of the present invention onto the surface of the body, i.e. skin, scalp, hair, nails and the like, preferably on the surface affected by the infection.

As used herein the phrase "transdermal administration" refers to administration of the compositions of the present invention across the skin for systemic administration (e.g. via transdermal patches or by transdermal implants). The transdermal administration is typically effected in close proximity to the target site, however, transdermal administration may be carried out in any anatomical location as seen fit by one of ordinary skill in the art.

As used herein the phrase "subdermal administration" refers to administering the compositions of the present invention under the skin (i.e. completely buried in the skin, e.g. via subdermal implants). The subdermal administration is typically effected in close proximity to the target site, however, subdermal administration may be carried out in any anatomical location as see fit by one of ordinary skill in the art.

Compositions of the present invention may be manufactured by processes well known in the art, e.g., by means of conventional mixing, dissolving, granulating, dragee-making, levigating, emulsifying, encapsulating, entrapping or lyophilizing processes.

Compositions for use in accordance with some embodiments of the invention thus may be formulated in conventional manner using one or more physiologically acceptable carriers comprising excipients and auxiliaries, which facilitate processing of the active ingredients into preparations which, can be used cosmetically or pharmaceutically. Proper formulation is dependent upon the route of administration chosen.

In addition, a dose can be formulated in tissue cultures systems (e.g. ex-vivo systems) or in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the infection) and the responsiveness of the subject to treatment, dosing can be of a single or a plurality of administrations, with course of treatment lasting from several days to several weeks, several months or several years, or until cure is effected or diminution of the infection is achieved. Alternatively, the compositions are administered in order to prevent occurrence of an infection in a subject at risk of developing an infection (e.g. a subject suffering from a chronic inflammatory disease). The compositions may be administered for prolonged periods of time (e.g. several days, several weeks, several months or several years) as to prevent occurrence of an infection.

According to an embodiment of the present invention, the compositions of the present invention are administered at least once a day. According to another embodiment, the compositions are administered twice a day, three times a day or more.

According to an embodiment of the present invention, administering is effected chronically.

According to another embodiment, administering is effected for at least about 10 days, 12 days, 14 days, 16 days, 18 days, 21 days, 24 days, 27 days, 30 days, 60 days, 90 days or more.

The amount of a composition to be administered will, of course, be dependent on the subject being treated, the severity of the affliction, the manner of administration, the judgment of the prescribing physician, etc.

The compositions of the present invention may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an ampule, a dispender, an adhesive bandage, a non-adhesive bandage, a wipe, a baby wipe, a gauze, a pad and a sanitary pad.

The present formulation may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients (i.e. herbal extracts or prevalent molecules therefrom in compositions of the present invention) while preserving their biological activity and prolonging its half-life.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

EXAMPLES

Example 1

Synergistic Inhibitory Effect of Combinations of *Rheum Palmatum*, *Sanguisorba Officinalis* and *Chrysanthemum Indicum* Herbal Extracts on Herpes Simplex Virus Infection of Vero Cells A study was conducted to test the potency of *Rheum palmatum*, *Sanguisorba officinalis* and *Chrysanthemum indicum* herbal extracts to inhibit infection of African green monkey kidney epithelial cells (Vero cells) by Herpes Simplex Virus type 1 (HSV-1).

Materials and Methods

Cells and viruses: Green monkey kidney cells (Vero cells) were grown in Dulbecco's Modified Eagle's Medium (DMEM) containing penicillin-streptomycin and 10% Foetal Bovine Serum (FBS). Cells were incubated at 37° C. in a 5% $CO_2$ incubator. The virus used in this study was HSV-1 that carries a gene for enhanced yellow fluorescent protein (herein referred to as EYFP-HSV-1). Viral stock was prepared by infecting Vero cells with EYFP-HSV-1 for 24 hours, until all the cells displayed cytopathic effect. Then both cells and medium were harvested and aliquots stored frozen until used. The viral stock titer was determined using the plaque assay method, in brief: 10-fold dilutions of the virus stock were prepared and added to pre-seeded monolayers of Vero cells in 6-well plates. Following one hour incubation at 37° C. 5% $CO_2$, the cells were overlaid with 1% methylcellulose and further incubated at 37° C. 5% $CO_2$ for 72 hours, at which point the methycellulose was removed, cells stained (with a Coomassie blue preparation), plaques counted, and viral stock titer calculated.

Viral replication assay: Vero cells were seeded ($1 \times 10^4$ cells/well) in black 96-well plates and incubated at 37° C. 5% $CO_2$ overnight. The following day cells were infected with EYFP-HSV-1 at multiplicity of infection (MOI) of 0.01 in absence or presence of herbal extracts at required dilutions. Following a one hour absorption period the inoculum was removed and replaced with fresh medium without/with herbal extracts at required dilutions, followed by further incubation at 37° C. 5% $CO_2$. Acyclovir, a synthetic analogue of guanosine established as an antiviral compound, was used as positive control. At 48 hours post infection, plates were inspected using a bright field microscope and cell viability assessed. Fluorescence, a measure of viral replication, was measured by two methods: 1) fluorescence images were acquired using the Nikon Eclipse Ti-E epifluorescence inverted microscope; 2) fluorescence intensities were measured using a Gen5 (BioTek) plate reader.

Data analysis: Individual fluorescence values were plotted against concentrations of the test items. Model curves were constructed based on a four-parameter logistic equation, which defines a sigmoidal curve that relates response y to dose x.

$$y = d + \frac{a-d}{1 + \left(\frac{x}{IC_{50}}\right)^{-b}} \qquad \text{Equation 1}$$

The parameters d and a are the maximum and minimum asymptotes, $IC_{50}$ corresponds to the dose for the inflection point and b is a slope factor. Model curves were fitted to the data points using Microsoft Excel's "Solver" procedure to minimize the sum-squared fluorescence differences between data points and their respective curves, using data from the same assay plate to fit common asymptotes. Standard errors of the $IC_{50}$ estimates were calculated from the intercepts of logit linear regressions $$\left(\log \text{conc. vs. } \log \frac{d-y}{y-a}\right).$$

Measured inhibitions were calculated from the fluorescence signal (y):

$$I = \frac{d-y}{d-a}.$$

Standard deviations and standard errors of inhibition were estimated from the standard deviations between replicates. Doses expected to give different inhibition levels (e.g. $IC_{30}$ for 30% inhibition, $IC_{60}$ for 60% inhibition, etc.) were calculated from the inverse of Equation 1.

Results

FIGS. 1 through 4 present test results for three herbal extracts from *Rheum palmatum*, *Sanguisorba officinalis* and *Chrysanthemum indicum*. Vero cells were infected with EYFP-HSV-1, an HSV-1 strain expressing yellow fluorescence protein, thereby allowing virus growth to be estimated by measuring fluorescence levels. Cells were either non-treated or treated with various concentrations of *Rheum palmatum, Sanguisorba officinalis* and *Chrysanthemum indicum* or combinations thereof. Cell viability was assessed by bright field microscopy. At herbal extract concentrations at which fluorescence was recorded, no adverse effect on cell viability was observed. Acyclovir dose-response curve showed a half maximal inhibitory concentration ($IC_{50}$) =0.171±0.015 µg/ml, which is in accordance with published $IC_{50}$ values for acyclovir, thus validating the assay.

Figure 4:
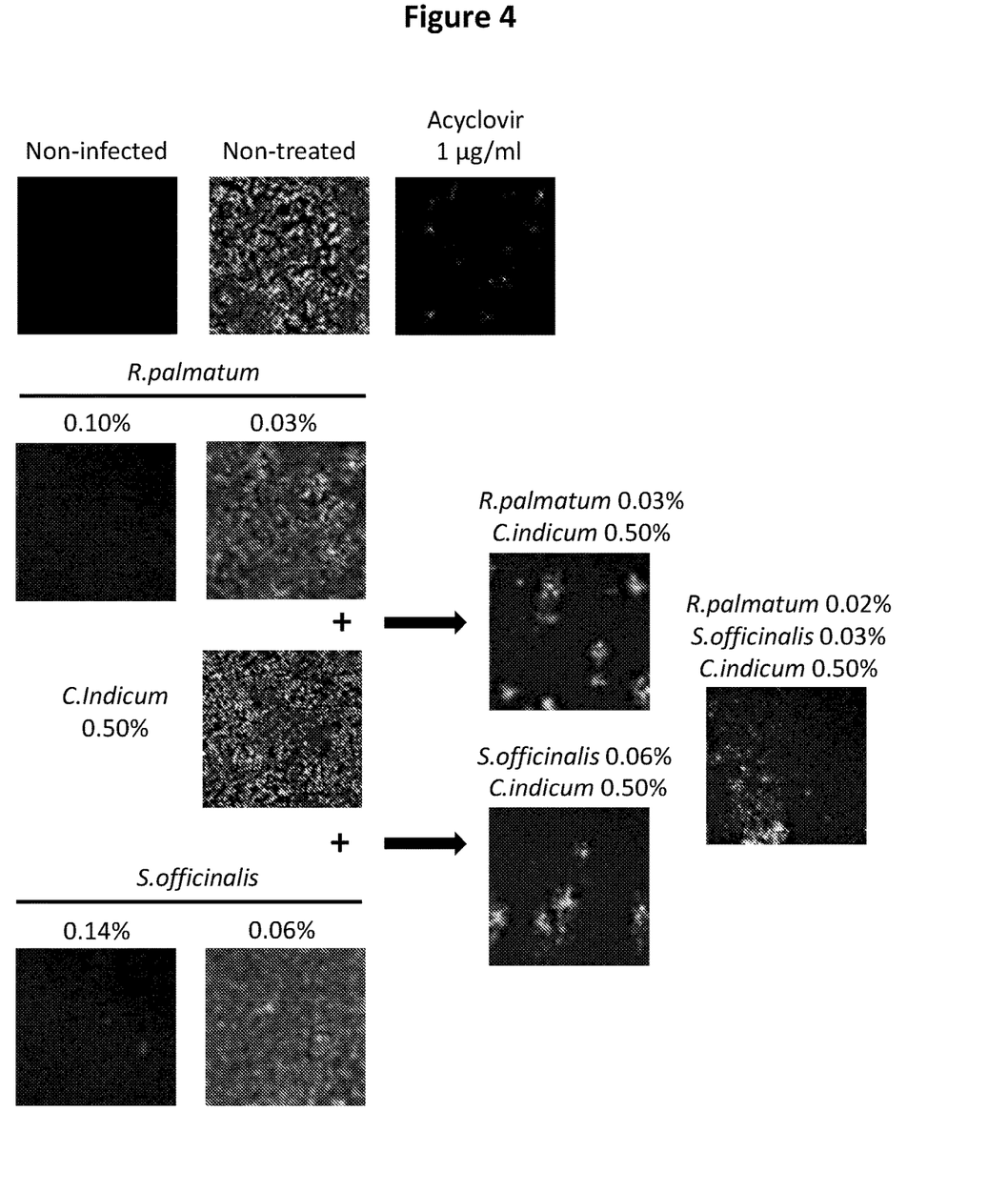
FIG. 4 presents representative fluorescent microscopy images that illustrate the synergistic inhibitory effect of the *Rheum palmatum, Sanguisorba officinalis* and *Chrysanthemum indicum* herbal extract combinations on herpes simplex virus-1 infection of Vero cells.

The *Rheum palmatum* extract on its own inhibited viral growth with $IC_{50}$=0.0355%±0.0011%. Extracts of *Rheum* varieties are known to have anti-HSV activity. *Chrysanthemum indicum* extract was not found to inhibit viral growth when tested at concentrations up to 0.5% (higher concentrations proved toxic to the cells). To test the combined effect of these two herbal extracts, the *Rheum palmatum* extract was diluted in cell culture medium containing 0.5% *Chrysanthemum indicum* extract. Thus, the concentration of *Chrysanthemum indicum* extract remained constant (0.5%) while a dilution series was created for *Rheum palmatum*. The combination with *Chrysanthemum indicum* extract resulted in the potency of *Rheum palmatum* extract increasing, such that the $IC_{50}$ was reduced to 0.0281%±0.0012% (FIG. 1), a significant (p<0.05) reduction. Representative fluorescent microscopy images are shown in FIG. 4. Taken together these data show synergistic anti-HSV-1 activity of *Rheum palmatum* and *Chrysanthemum indicum* extracts.

The *Sanguisorba officinalis* extract inhibited viral growth with $IC_{50}$=0.0695%±0.0019%. Extracts of *Sanguisorba* varieties are known to have anti-viral activity. To test the combined effect *Sanguisorba officinalis* and *Chrysanthemum indicum* herbal extracts, the *Sanguisorba officinalis* extract was diluted in cell culture medium containing 0.5% *Chrysanthemum indicum* extract. Thus, the concentration of *Chrysanthemum indicum* extract remained constant (0.5%) while a dilution series was created for *Sanguisorba officinalis*. This resulted in increased potency of the *Sanguisorba officinalis* extract such that the $IC_{50}$ was reduced to 0.0486%±0.0016% (FIG. 2), a significant (p<0.05) reduction. Representative fluorescent microscopy images are shown in FIG. 4. Taken together these data show synergistic anti-HSV-1 activity of *Sanguisorba officinalis* and *Chrysanthemum indicum* extracts.

Figure 1:
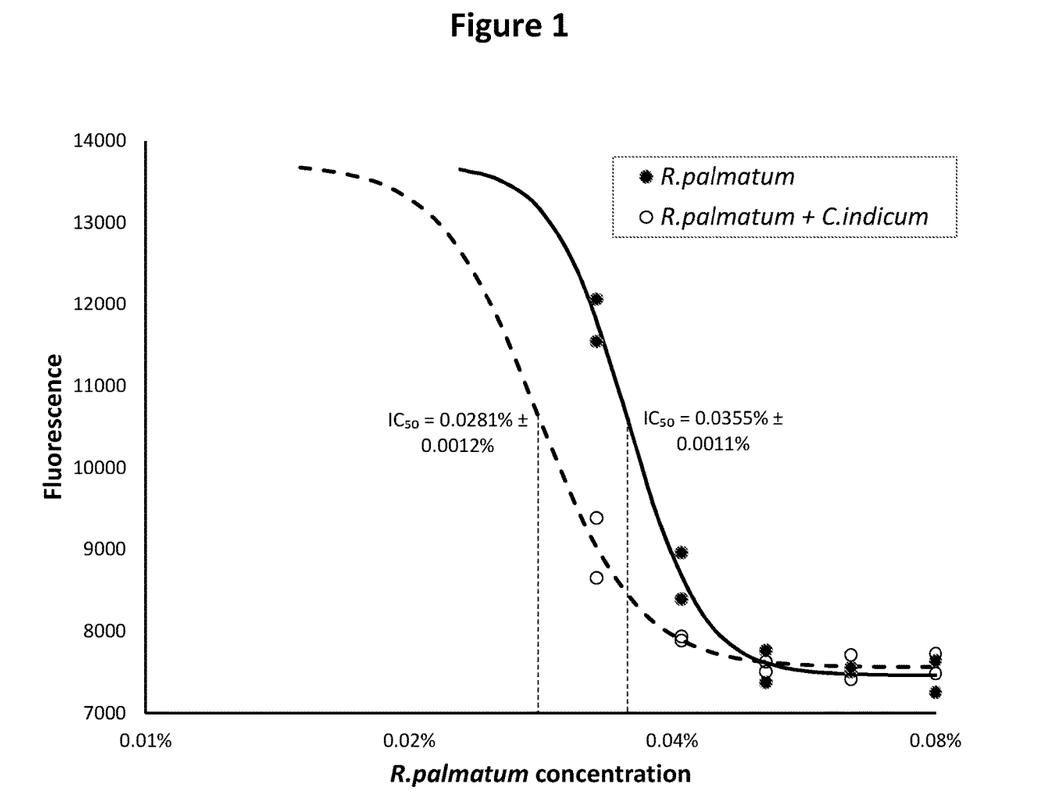
FIG. 1 presents the synergistic inhibitory effect of a formulation comprising *Rheum palmatum* and *Chrysanthemum indicum* herbal extract combinations on herpes simplex virus-1 infection of Vero cells.
Figure 2:
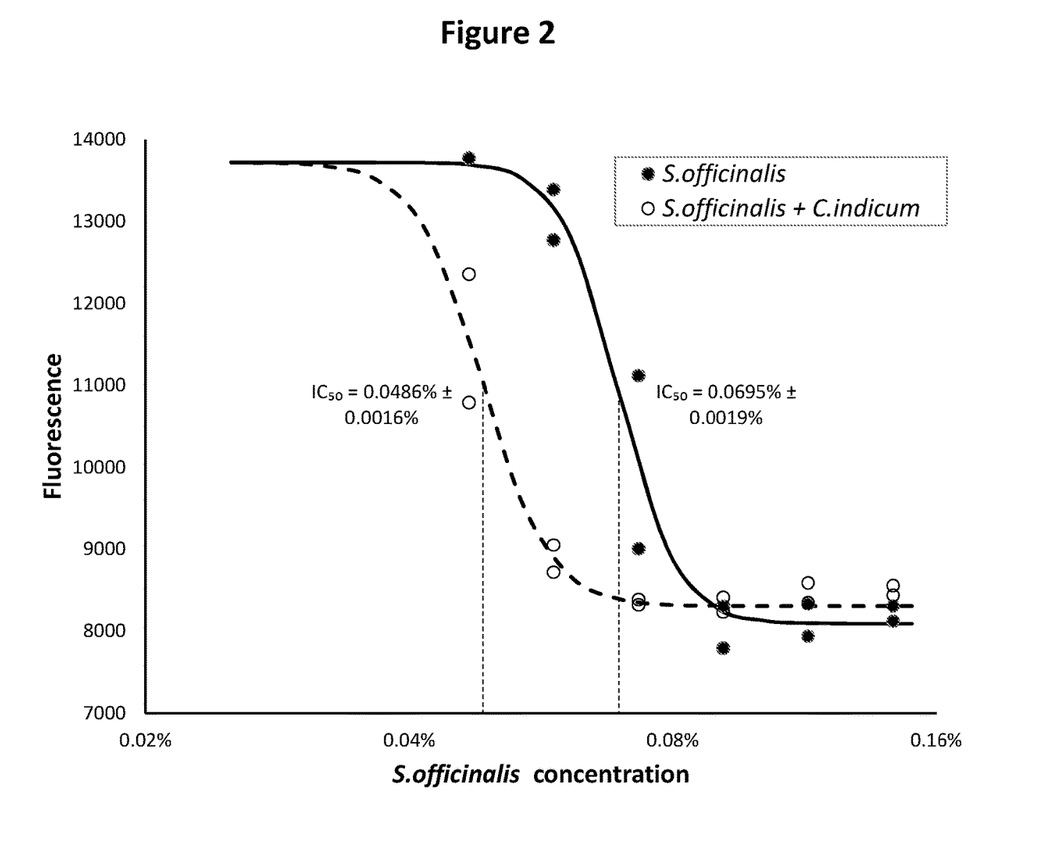
FIG. 2 presents the synergistic inhibitory effect of a formulation comprising *Sanguisorba officianalis* and *Chrysanthemum indicum* herbal extract combinations on herpes simplex virus-1 infection of Vero cells.
Figure 3:
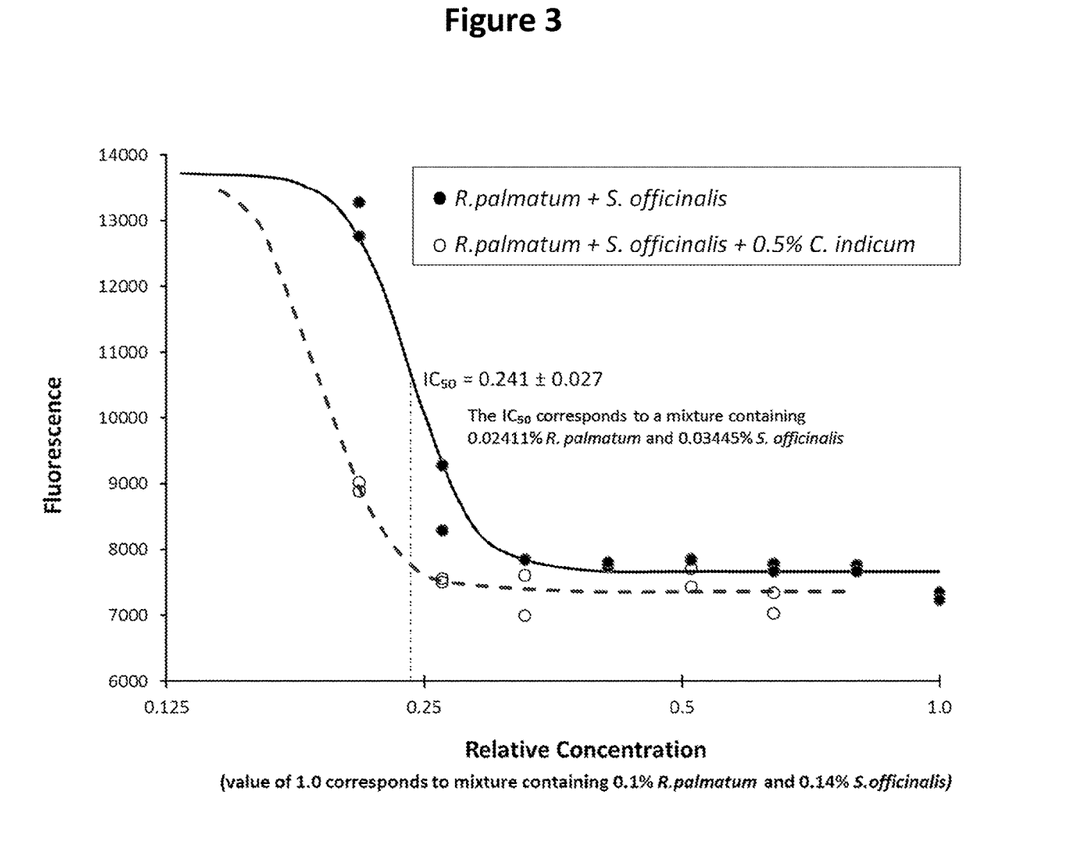
FIG. 3 presents the synergistic inhibitory effect of a formulation comprising *Rheum palmatum, Sanguisorba officianalis* and *Chrysanthemum indicum* herbal extract combinations on herpes simplex virus-1 infection of Vero cells.

The anti-HSV-1 activity of *Rheum palmatum* extract in combination with *Sanguisorba officinalis* extract with/without the further addition of *Chrysanthemum indicum* extract, was also examined. The extracts of *Rheum palmatum* and *Sanguisorba officinalis* were combined and diluted in cell-culture medium. This combination achieved 50% viral growth inhibition at *Rheum palmatum* and *Sanguisorba officinalis* extract concentrations of 0.0241±0.0007% and 0.0344±0.0009%, respectively (FIG. 3). Although these $IC_{50}$ values are lower than those for the extracts individually, analysis of the results does not indicate a synergistic effect at this ratio. To test the combined effect of all three herbal extracts, the *Rheum palmatum* and *Sanguisorba officinalis* combination was diluted in cell culture medium containing 0.5% *Chrysanthemum indicum*. Thus the concentration of *Chrysanthemum indicum* remained constant (0.5%) while a dilution series was created for *Rheum palmatum* and *Sanguisorba officinalis*. Combining all three herbal extracts resulted in increased inhibition of viral growth (FIG. 3). This is evident in the shift of the activity curve towards the lower concentrations of *Rheum palmatum* and *Sanguisorba officinalis*. At concentrations of 0.021% and 0.030% of *Rheum palmatum* and *Sanguisorba officinalis*, respectively, the fluorescence measured was closed to maximal, whereas in the presence of *Chrysanthemum indicum* fluorescence measured drop drastically indicating viral growth inhibition that was too strong to allow $IC_{50}$ values to be calculated. Representative fluorescent microscopy images are shown in FIG. 4. Taken together these data show synergistic anti-HSV-1 activity of *Rheum palmatum, Sanguisorba officinalis* and *Chrysanthemum indicum* extracts.

Conclusions

Herbal extracts of *Rheum palmatum* and *Sanguisorba officinalis* are efficacious for inhibiting HSV-1 replication. In addition, various combinations of *Rheum palmatum* and *Sanguisorba officinalis* extracts with *Chrysanthemum indicum* demonstrate a synergistic effect in inhibiting HSV-1 replication.

Example 2

Synergistic Inhibitory Effect of *Rheum Palmatum* and *Chrysanthemum Indicum* Herbal Extracts and Acyclovir Combinations on Herpes Simplex Virus Infection of Vero Cells A study was conducted to test the potency of *Rheum palmatum* and *Chrysanthemum indicum* herbal extracts in combination with acyclovir to inhibit infection of African green monkey kidney epithelial cells (Vero cells) by Herpes simplex virus type 1 (HSV-1).

Materials and Methods

Same as in Example 1

Results

FIGS. 5 through 8 present test results for combinations of *Rheum palmatum* and *Chrysanthemum indicum* herbal extracts and acyclovir. Vero cells were infected with EYFP-HSV-1, an HSV-1 strain expressing yellow fluorescent protein, thereby allowing virus growth to be estimated by measuring fluorescence levels. Cells were either non-treated or treated with various concentrations of *Rheum palmatum* extract, *Chrysanthemum indicum* extract and acyclovir or combinations thereof. Cell viability was assessed by bright field microscopy. At herbal extract/acyclovir concentrations at which fluorescence was recorded, no adverse effect on cell viability was observed. Acyclovir dose-response curve showed $IC_{50}$=0.126±0.014, which is in accordance with published $IC_{50}$ values for acyclovir, thus validating the experimental results.

Figure 5:
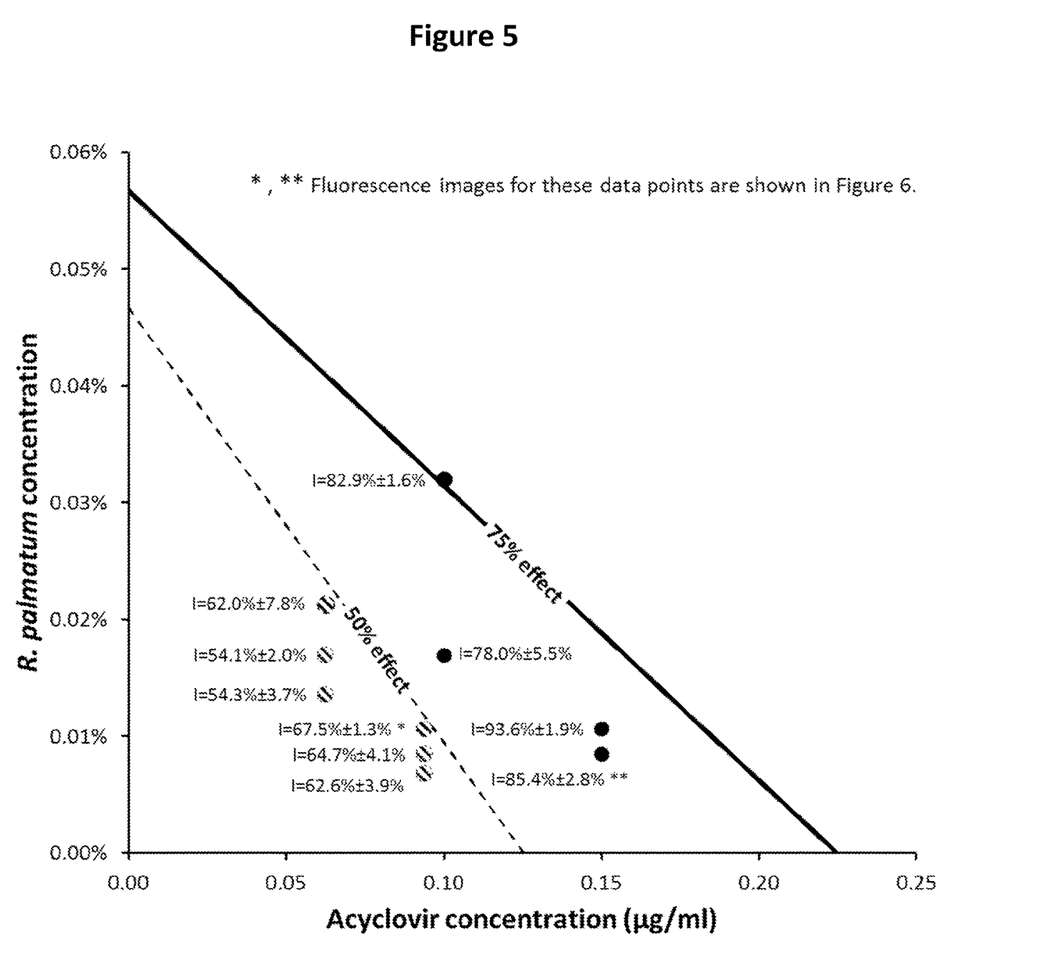
FIG. 5 presents the synergistic inhibitory effect of a formulation comprising *Rheum palmatum* herbal extract and acyclovir on herpes simplex virus-1 infection of Vero cells.
Figure 6:
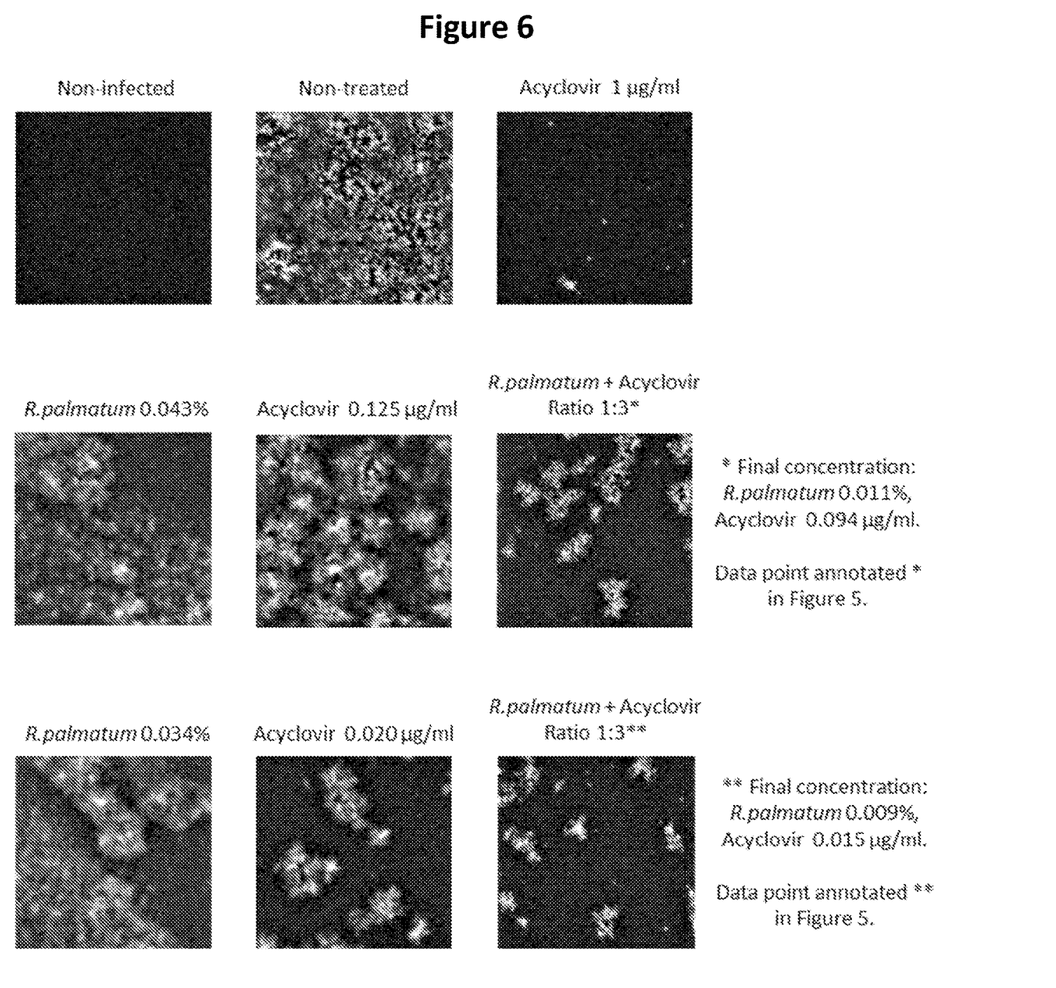
FIG. 6 presents representative fluorescent microscopy images that illustrate the synergistic inhibitory effect of formulations *of Rheum palmatum* herbal extract and acyclovir on herpes simplex virus-1 infection of Vero cells.

Different concentrations of *Rheum palmatum* extract and acyclovir were tested singly or in combination. Data were analysed using isobologram analysis, the most commonly used and accepted form of analysis for drug combination experiments. In FIG. 5, the straight-line isobol (additivity line, labelled "50% effect" in the figure) connects the $IC_{50}$ concentrations for *Rheum palmatum* extract on the vertical axis to the $IC_{50}$ for acyclovir on the horizontal axis. Similarly, the isobol (labelled "75% effect") connects the $IC_{75}$ concentrations. The individual data points correspond to tested combinations, with the X-and Y-coordinates for each data point corresponding to acyclovir and *Rheum palmatum* concentrations, respectively; each data point is annotated with the resulting inhibition (average±standard error) measured for that combination. Any data point below an isobol but with higher inhibitory effect, corresponds to a Combination Index (CI) <1 that is defined as synergy. Representative fluorescent microscopy images are shown in FIG. 6. Taken together these data shows synergistic anti-HSV-1 activity of *Rheum palmatum* and acyclovir.

Figure 7:
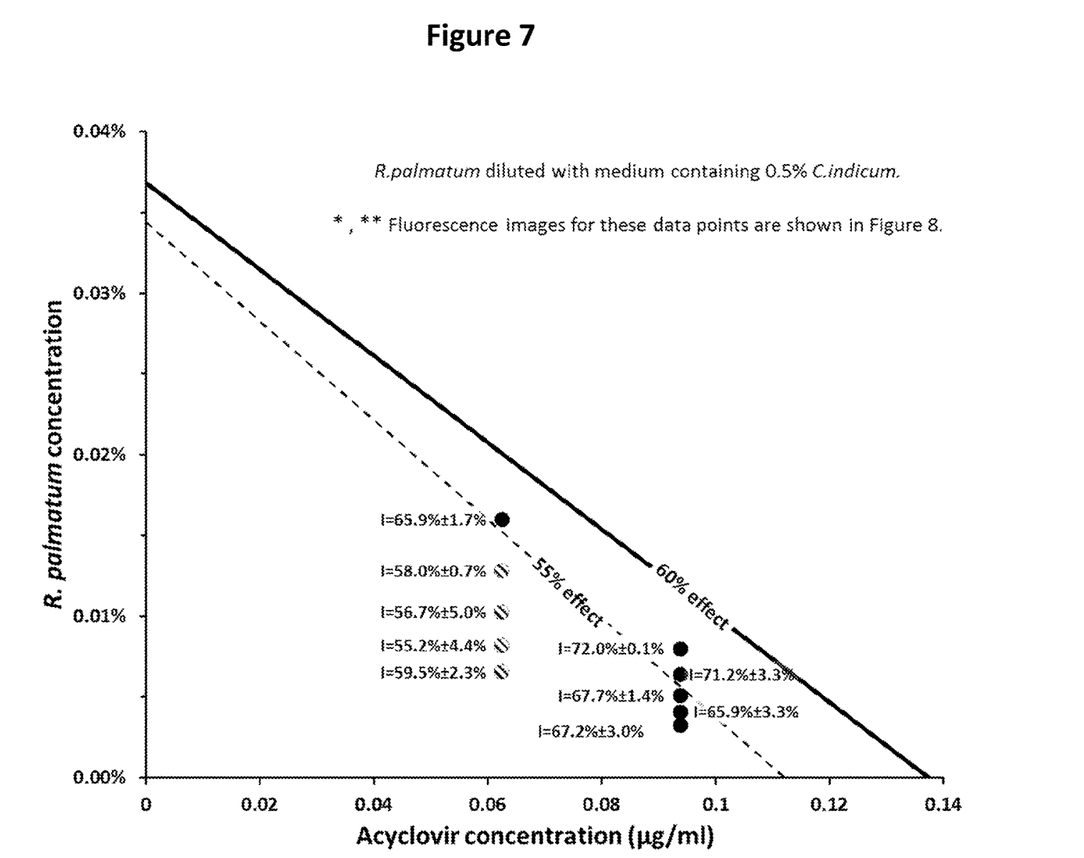
FIG. 7 presents the synergistic inhibitory effect of a formulation comprising *Rheum palmatum* and *Chrysanthemum indicum* herbal extracts together with acyclovir on herpes simplex virus-1 infection of Vero cells.
Figure 8:
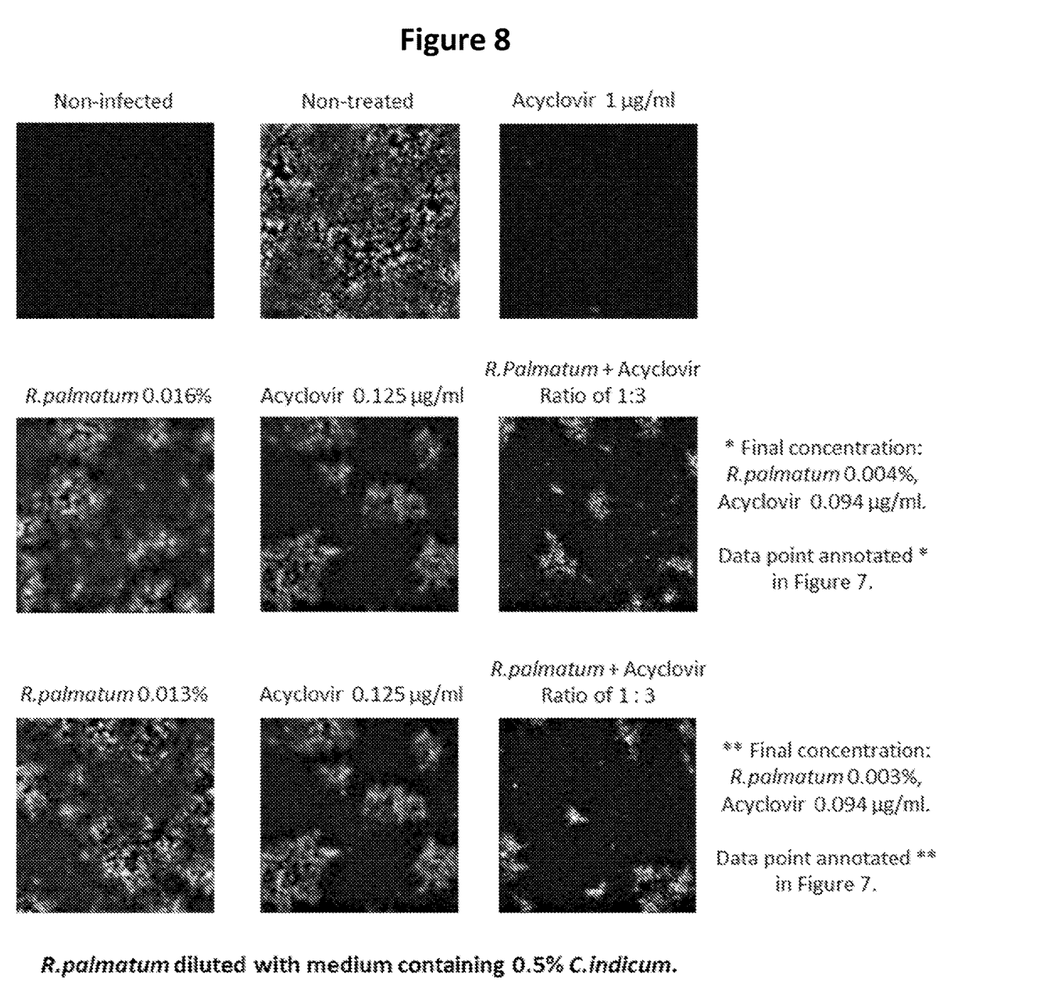
FIG. 8 presents representative fluorescent microscopy images that illustrate the synergistic inhibitory effect of a formulation comprising *Rheum palmatum* and *Chrysanthemum indicum* herbal extracts and acyclovir on herpes simplex virus-1 infection of Vero cells.

In addition, the combined effect of *Rheum palmatum* and *Chrysanthemum indicum* herbal extracts together with acyclovir was examined. Different concentrations of acyclovir and *Rheum palmatum* extract, diluted in cell culture medium containing 0.5% *Chrysanthemum indicum*, were tested. Isobologram analysis shows the combination of the herbal extracts with acyclovir resulted in synergistic inhibition of viral growth (FIG. 7). Representative images are shown in FIG. 8. Taken together these data show synergistic anti-HSV-1 activity of *Rheum palmatum, Chrysanthemum indicum* and acyclovir combination.

Conclusions

*Rheum palmatum* singly and *Rheum palmatum* and *Chrysanthemum indicum* mixtures in combination with acyclovir demonstrate a synergistic effect in inhibiting HSV-1 replication.

Example 3

TABLE 2

Formulation for treating herpesvirus infections (gel)

| | |
|---|---|
| Water (Aqua) | |
| Glycerin | Humectant |
| Propanediol | Humectant |
| Methylpropanediol (and) Caprylyl Glycol (and) Phenylpropanol | Preservative |
| *Crysantemum Indicum* Flower Extract | Skin conditioner |
| Sodium Polyacrylate(and) Ethylhexyl Stearate (and) Trideceth-6 | Thickening agent |
| *Rheum Palmatum* Root Extract | Skin conditioner |
| *Sanguisorba Officinalis* Root Extract | Skin conditioner |
| Allantoin | Skin conditioner |

Example 4

Case Studies

Figure 9:
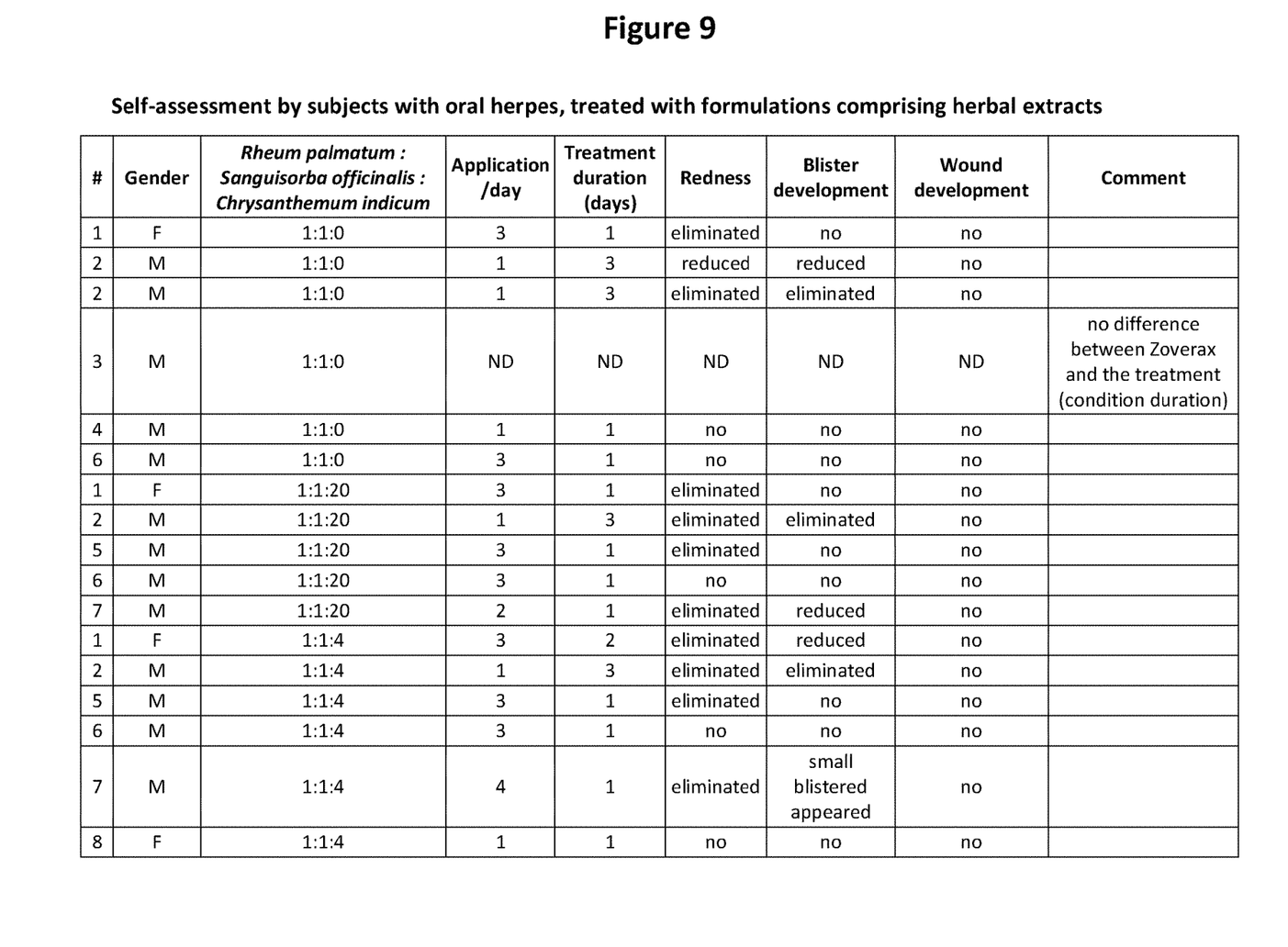
FIG. 9 presents the self-assessment by subjects suffering from oral herpes, treated with formulations comprising different combinations of *Rheum palmatum, Sanguisorba officianalis* and *Chrysanthemum indicum* herbal extracts.

Eight adult volunteers were requested to apply topical formulations comprising herbal extracts of *Rheum palmatum, Sanguisorba officinalis* and *Chrysanthemum indicum* combined in different ratios and at individual extract concentrations between 0.1%-5%. The subjects were asked to apply the product during a breakout of oral herpes and to report their assessment. Details and results are provided in FIG. 9. All volunteers experienced complete or partial relief of oral herpes symptoms following application of the formulations.

The invention claimed is:

1. A formulation consisting of extracts of *Rheum palmatum, Chrysanthemum indicum* and *Sanguisorba officinalis* and a pharmaceutically acceptable carrier in an effective amount to treat a herpesvirus infection and/or prevent diseases resulting therefrom in humans.

2. The formulation of claim 1, wherein the formulation is a topical formulation.

3. The formulation according to claim 2, wherein the pH of the formulation is between 4.0 and 7.0.

4. The formulation according to claim 1, wherein the combined concentration of the herbal extracts in the formulation is between 0.01% w/w and 50% w/w.

5. A method of treating herpesvirus infections and/or preventing diseases resulting from herpesvirus infections, comprising administering the formulation according to claim 1 to a human patient in need thereof.

6. The method according to claim 5, wherein the formulation is administered once, twice, three or more times a day.

7. The method according to claim 5, wherein the formulation is administered for one, two, three or more days.

8. The method of claim 5, wherein the herpesvirus infection is an HSV-1 infection.

9. The method of claim 5, wherein the herpesvirus infection is an HSV-2 infection.

10. The method of claim 5, wherein the herpesvirus infection is a VZV infection.

11. The method of claim 5, further comprising administering the formulation in conjunction with an antiviral agent.

12. The method of claim 11, wherein the antiviral agent is acyclovir.

* * * * *